United States Patent
Servidio

(10) Patent No.: US 11,596,519 B2
(45) Date of Patent: Mar. 7, 2023

(54) HINGE KNEE ASSEMBLY GUIDE

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 300 days.

(21) Appl. No.: 16/930,838

(22) Filed: Jul. 16, 2020

(65) Prior Publication Data

US 2021/0015621 A1 Jan. 21, 2021

Related U.S. Application Data

(60) Provisional application No. 62/874,692, filed on Jul. 16, 2019.

(51) Int. Cl.
*A61F 2/38* (2006.01)
*A61F 2/46* (2006.01)
*A61F 2/30* (2006.01)

(52) U.S. Cl.
CPC ............ *A61F 2/3845* (2013.01); *A61F 2/389* (2013.01); *A61F 2/3859* (2013.01); *A61F 2/461* (2013.01); *A61F 2002/30112* (2013.01)

(58) Field of Classification Search
CPC ...... A61F 2/3845; A61F 2/3859; A61F 2/389; A61F 2/461; A61F 2002/30112; A61F 2/384; A61F 2/385
See application file for complete search history.

(56) References Cited

U.S. PATENT DOCUMENTS

| | | | |
|---|---|---|---|
| 3,837,009 A | 9/1974 | Walker | |
| 4,136,405 A * | 1/1979 | Pastrick | A61F 2/384 |
| | | | 623/20.25 |
| 4,219,893 A | 9/1980 | Noiles | |
| 4,262,368 A | 4/1981 | Lacey | |
| 4,301,553 A | 11/1981 | Noiles | |
| 4,358,859 A | 11/1982 | Schurman et al. | |
| 5,011,496 A | 4/1991 | Forte et al. | |

(Continued)

FOREIGN PATENT DOCUMENTS

FR 2980104 B1 12/2013

OTHER PUBLICATIONS

Modular Rotating Hinge Knee System, Stryker Howmedica Osteonics, 5 pages.

(Continued)

*Primary Examiner* — Yashita Sharma
(74) *Attorney, Agent, or Firm* — Lerner, David, Littenberg, Krumholz & Mentlik, LLP

(57) ABSTRACT

A total knee prosthesis system that includes a guide having first and second wedges each having a thickness configured to be located between the tibial and femoral component. When the first and second wedges are located between the tibial and femoral component, the first and second wedges align the first axle opening of the tibial component with the second axle opening of the femoral component for receipt of an axle. The guide includes a guide recess extending between the first and second wedges and a post extending into the guide recess. The guide also includes a bridge connected to and extending between the first and second wedges such that the bridge at least partially defines the guide recess.

15 Claims, 3 Drawing Sheets

(56) References Cited

U.S. PATENT DOCUMENTS

| | | |
|---|---|---|
| 5,358,527 A | 10/1994 | Forte |
| 5,370,701 A | 12/1994 | Finn |
| 5,413,607 A | 5/1995 | Engelbrecht et al. |
| 5,766,257 A | 6/1998 | Goodman et al. |
| 5,800,552 A | 9/1998 | Forte |
| 5,824,096 A | 10/1998 | Pappas et al. |
| 5,954,770 A | 9/1999 | Schmotzer et al. |
| 6,013,103 A | 1/2000 | Kaufman et al. |
| 6,447,549 B1 | 9/2002 | Taft |
| 6,719,800 B2 | 4/2004 | Meyers et al. |
| 6,962,607 B2 | 11/2005 | Gundlapalli et al. |
| 7,387,644 B2 | 6/2008 | Beynnon et al. |
| 7,572,292 B2 | 8/2009 | Crabtree et al. |
| 7,591,855 B2 | 9/2009 | Keller |
| 7,658,767 B2 | 2/2010 | Wyss |
| 7,695,520 B2 | 4/2010 | Metzger et al. |
| 7,708,782 B2 | 5/2010 | Burstein et al. |
| 7,871,442 B2 | 1/2011 | Servidio |
| 7,918,893 B2 | 4/2011 | Romeis et al. |
| 7,998,218 B1 | 8/2011 | Brown |
| 8,163,028 B2 * | 4/2012 | Metzger ............... A61F 2/385 623/20.15 |
| 8,268,006 B2 | 9/2012 | Meyers et al. |
| 8,328,873 B2 | 12/2012 | Metzger et al. |
| 8,382,848 B2 | 2/2013 | Ries et al. |
| 8,523,950 B2 | 9/2013 | Dees et al. |
| 8,545,570 B2 | 10/2013 | Crabtree et al. |
| 8,545,571 B2 | 10/2013 | Collazo et al. |
| 8,568,485 B2 | 10/2013 | Ries et al. |
| 8,617,250 B2 | 12/2013 | Metzger |
| 8,628,579 B2 | 1/2014 | Ries et al. |
| 2004/0249467 A1 | 12/2004 | Meyers et al. |
| 2011/0270403 A1 | 11/2011 | Ries et al. |
| 2012/0271427 A1 | 10/2012 | Serafin, Jr. et al. |
| 2012/0330430 A1 | 12/2012 | Meyers et al. |
| 2013/0190883 A1 | 7/2013 | Collard et al. |
| 2013/0325135 A1 | 12/2013 | Crabtree, Jr. et al. |
| 2014/0025172 A1 | 1/2014 | Lucas et al. |
| 2014/0025174 A1 | 1/2014 | Lucas et al. |
| 2014/0114318 A1 | 4/2014 | May et al. |
| 2017/0035572 A1 * | 2/2017 | Servidio ............... A61F 2/3845 |

OTHER PUBLICATIONS

Resurfacing Distal Femur, Orthopaedic Salvage System, Biomet Orthopedics Inc, 32 pages.

S-ROM Noiles Rotating Hinge, Surgical Technique, DePuy, 60 pages.

Zimmer NexGen Rotating Hinge Knee Primary/Revision Surgical Technique, 114 pages.

* cited by examiner

HINGE KNEE ASSEMBLY GUIDE

CROSS-REFERENCE TO RELATED APPLICATIONS

The present application claims the benefit of the filing date of U.S. Provisional Patent Application No. 62/874,692, filed Jul. 16, 2019, the disclosure of which is hereby incorporated herein by reference.

BACKGROUND OF THE INVENTION

A natural knee includes a distal femur, proximal tibia, and patella. The distal femur and proximal tibia comprise a tibiofemoral joint, and the distal femur and patella comprise a patellofemoral joint. Soft tissue, such as ligaments and tendons, help stabilize these joints throughout flexion of the knee. However, the natural knee can become damaged or diseased. For example, osteoarthritis can destroy articular cartilage within the tibiofemoral and/or patellofemoral joints producing painful bone-on-bone articulation and malalignment of the knee.

Surgery may be indicated to treat complications of such damage or disease. This may involve resecting portions of the distal femur, proximal tibia, and patella and replacing the resected bone with one or more prostheses. Surgery to replace the patellofemoral and tibiofemoral joints is commonly referred to as total knee arthroplasty ("TKA") or total knee replacement.

In many circumstances, damage extends beyond the articular cartilage and bone further complicating a TKA procedure. For example, malalignment of the knee caused by osteoarthritis can impose excess stress on stabilizing soft tissue, which may result in damage and/or laxity of such structures and instability of the knee. Without resolution, such damage and/or laxity can compromise the replaced tibiofemoral and patellofemoral joints and reduce patient satisfaction.

Certain categories of prostheses have been developed to address soft tissue instability. One such category is a posterior stabilized ("PS") prosthesis. PS prostheses are often utilized to address posterior cruciate ligament deficiency in patients who otherwise have sufficient collateral ligament stability. Many of the existing PS prostheses offer tibiofemoral rotational freedom while providing stability during flexion to prevent femoral anterior subluxation. This is often achieved by a femoral cam and tibial post mechanism.

Another TKA prosthesis category is a hinge knee prosthesis. Hinge knee prostheses are typically indicated for patients that have significant stabilizing soft tissue deficiencies, particularly significant laxity or complete removal of the collateral ligaments. Hinge knee prostheses typically offer a one-degree-of-freedom hinge about which the knee flexes and extends. Such hinge is commonly comprised of an axle that connects a tibial component with a femoral component. Such axle is connected to these components by the surgeon during the procedure. However, in order to connect the axle to the femoral component and tibial component, the surgeon may need to hold both the femoral and tibial component in precise alignment so that the axle can be connected thereto, which may be complicated or difficult during surgery and may unnecessarily increase the time of the procedure as the surgeon deals with this assembly. Thus, further improvements are desirable.

BRIEF SUMMARY OF THE INVENTION

In a first aspect of the present disclosure, a total knee prosthesis system includes an axle, a tibial component, a femoral component, and a guide. The guide has first and second wedges that have a thickness configured to be located between the tibial component and the femoral component. When the first and second wedges are located between the tibial component and the femoral component, the first axle opening on the tibial component is aligned with the second axle opening of the femoral component such that the first and second axle openings can receive the axle. The first and second wedges may have curved proximal surfaces. The distal surface of the femoral component may have a plurality of portions, each defined by a different radius of curvature, such that the curved proximal surfaces of the wedges match the radius of curvature of a first of the plurality of portions of the distal surface of the femoral component Additionally, the tibial component includes a protruding portion extending from the baseplate and articular portions. The protruding portion includes a post opening configured to receive the post of the guide. When the guide is located between the tibial component and femoral component, the distal end surface of the guide engages the tibial component. The guide may have a fully seated position when located between the tibial and femoral components, and the fully seated position may only be achieved at one angle of flexion.

In another aspect of the present disclosure, a system for a total knee prosthesis includes a femoral component, a tibial component, an axle, a coupling component, and an assembly guide. The femoral component has first and second condylar portions, each defining a convex distal surface and further defining an intercondylar recess between the first and second condylar portions, and a first axle opening. The coupling component is coupled to the tibial component. A head portion extends from the tibial component and defines a second axle opening. The head portion is received within the intercondylar recess and the guide is interposed between the tibial component and femoral component. The thickness of the guide positions the femoral component such that the first axle opening coaxially aligns with the second axle opening so that the axle can be inserted into the first and second axle openings.

Continuing with this aspect, the tibial component may include a baseplate member and a polymer insert. The guide may include first and second guide portions and a guide recess extending therebetween. The guide recess may be configured to receive the head portion of the coupling component. The assembly guide may include a bridge connected to and extending between the first and second guide portions, there the bridge at least partially defines the guide recess. The guide may further include a post extending from the bridge and into the guide recess and the head portion may include a post opening configured to receive the post. The upper surface of the guide may include a first concave portion on the first guide portion and a second concave portion on the second guide portion. The first concave portion may have a radius of curvature equal to the radius of curvature of a convex distal surface of the first condylar portion. The distal surface of the first condylar portion may have an anterior section and a posterior section, the anterior section having a first radius of curvature, the posterior section having a second radius of curvature, where the first and second radii of curvature are different. The first concave portion of the guide may have a third radius of curvature equal to the second radius of curvature.

In a further aspect of the present disclosure, a method of assembling a hinge knee prosthesis includes positioning a head portion of a coupling component extending from a tibial component into an intercondylar recess of a femoral component. An alignment member is inserted between the tibial component and femoral component so that the alignment member positions the femoral component relative to the head portion such that the first axle opening of the femoral component aligns with a second axle opening of the coupling component. An axle is inserted into the first and second axle openings so as to hingedly connect the femoral component with the coupling component. The coupling component is removed from between the tibial component and the femoral component after the axle is inserted. Positioning the alignment member may include wedging the coupling component between the tibial component and femoral component so that an upper surface of the coupling component supports the femoral component and a thickness thereof aligns the first and second axle openings.

Additionally, the method may include the step of connecting a polymer insert to a baseplate of the tibial component. The polymer insert may have a concave proximal surface. Connecting the polymer insert to the baseplate may be performed prior to inserting the alignment member between the tibial and femoral component. The method may further include the step of inserting a bearing of the coupling component into an opening in the baseplate. Inserting the alignment member between the tibial component and femoral component may include the step of inserting a post of the alignment member into a post opening of the head portion. Inserting the alignment member between the tibial and femoral component may include contacting first and second condylar portions with respective first and second alignment portions of the alignment member.

BRIEF DESCRIPTION OF THE DRAWINGS

The features, aspects, and advantages of the present disclosure will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart, and the term "distal" means more distant from the heart. The term "inferior" means toward the feet, and the term "superior" means toward the head. The term "anterior means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that deviations from absolute are included within the scope of the term so modified.

Figure 1:
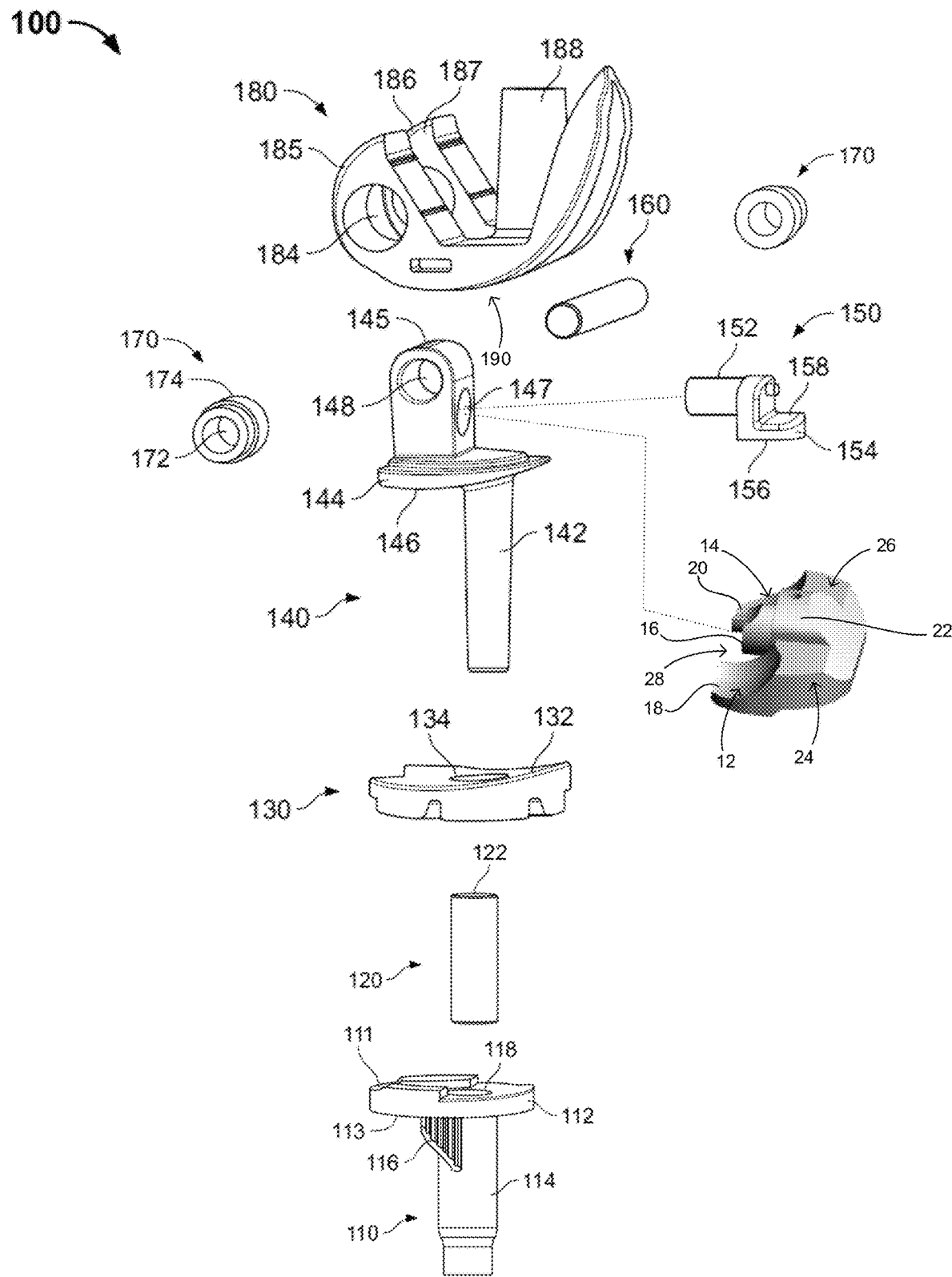
FIG. 1 is an exploded view of a total knee prosthesis system including an assembly guide.
Figure 2A:
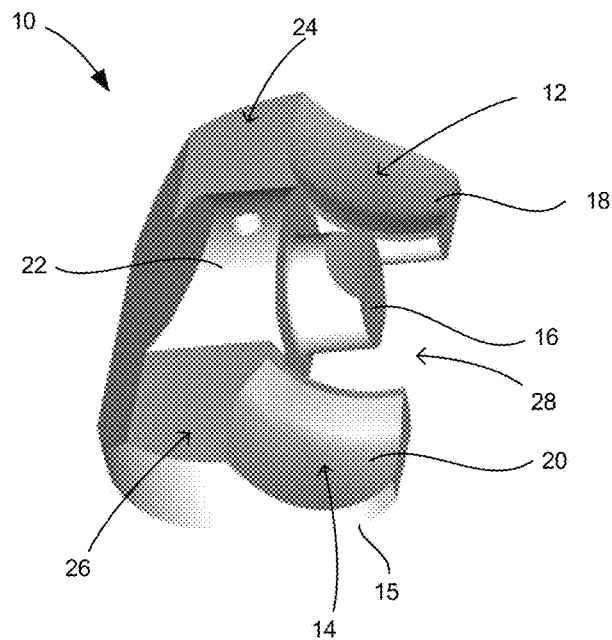
FIG. 2A is a perspective view of the assembly guide of FIG. 1 according to one embodiment of the present invention.
Figure 2B:
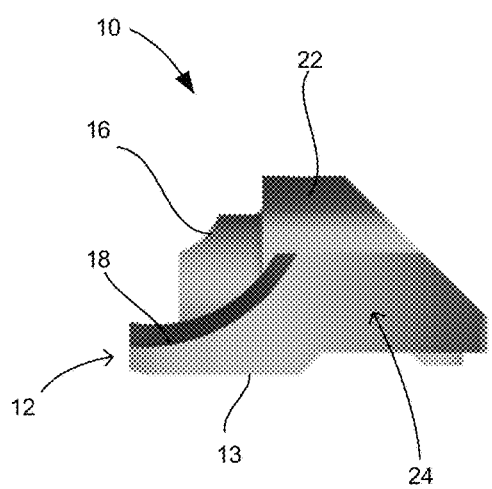
FIG. 2B is a side elevational view of the assembly guide of FIG. 2A.
Figure 2C:
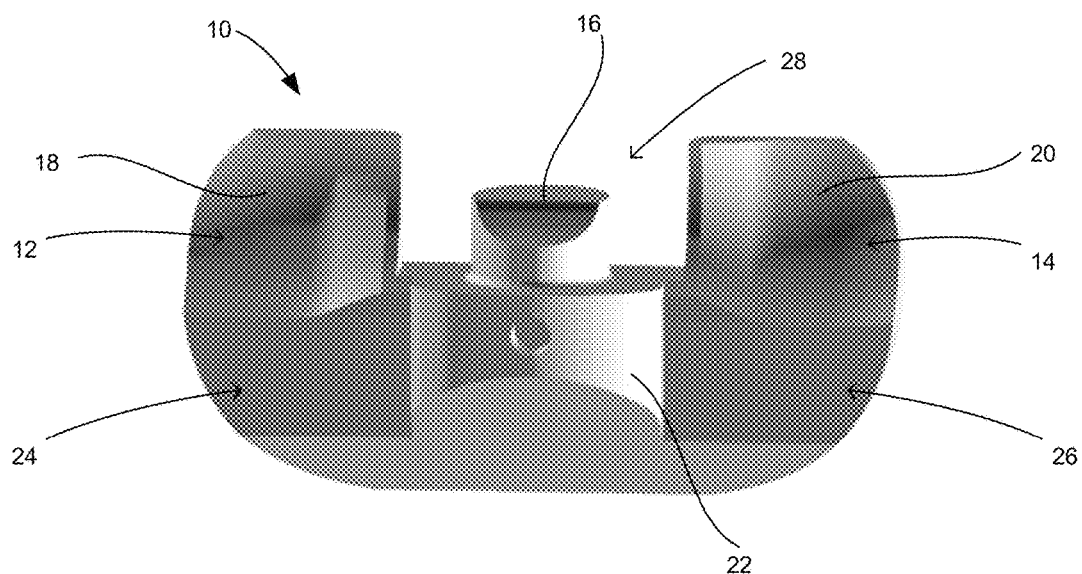
FIG. 2C is a top view of the assembly guide of FIG. 2A.

FIG. 1 depicts a hinge knee prosthesis system 100 according to one embodiment of the present invention. System 100 includes a tibial component or tibial assembly, axle 160, axle bushings 170, a femoral component 180, bumper 150, and alignment wedge 20. The tibial component, according to the depicted embodiment, generally includes a baseplate component 110, bearing bushing 120, tibial insert 130, and bearing component 140.

The baseplate component 110 may be comprised of various components that are separate components or integrally formed. In the depicted embodiment, baseplate component 110 includes a baseplate portion 112, stem 114, and keel 116. Baseplate portion 112 includes a proximal surface 111 that is configured to receive and retain tibial insert 130. Baseplate portion 112 also includes a distal or bone contact surface 113 disposed opposite proximal surface 111 that is configured to contact and rest upon a resected proximal tibia. As such, bone contact surface 113 is generally planar. However, in some embodiments, bone contact surface 113 may have curved ridges and/or a porous surface to facilitate secure registration with bone.

Stem or protruding portion 114 extends from baseplate portion 112 and may be sized to fit within an intramedullary canal of a tibia, which may or may not be reamed or otherwise resected to form a larger opening therein. Such fit may be a press fit. Alternatively, stem 114 may be sized to allow a bone cement mantle to be placed between stem 114 and the intramedullary canal and/or may have a porous outer surface to promote bone ingrowth or cement adhesion. An opening 118 extends through baseplate 112 and into stem 114. Opening 118 is sized to receive bearing bushing 120 therein.

Keel 116, which may be located on both lateral and medial sides of baseplate 112, extends between baseplate 112 and stem 114. Keel 116 helps prevent rotation of baseplate component 110 when implanted into bone.

Bearing bushing 120 is utilized when bearing component 140 is included as a separate component of baseplate component 110. Bearing bushing 120 is generally cylindrical and elongate and has an opening 122 extending therein along a longitudinal axis thereof. Opening 122 may extend entirely through bushing 120 or may extend partially therein. Opening 122 is sized to receive a bearing 142 of bearing component 140 (described further below) so that bearing 142 can rotate therein.

Tibial insert 130 includes an articular surface 132 that is concave in a sagittal plane such that articular surface 132 is higher at posterior and anterior extents thereof than at a location between such extents. Additionally, articular surface 132 at the anterior extent is generally higher or more proximal than articular surface 132 at the posterior extent. Also, the portion of articular surface 132 extending from the anterior extent toward the posterior extent generally has a steeper slope than the portion of articular surface 132 extending from the posterior extent toward the anterior extent. Moreover, an opening 134 extends through insert 130 sufficiently large to receive bearing 142 of bearing component 140 and for bearing 142 to rotate therein.

Bearing component 140 may be a separate component that is part of the tibial component, or bearing component may be integrally formed with baseplate component 110. Bearing component 140 generally includes an articular portion 144, a bearing 142 extending from articular portion 144, and a head portion 145 extending from articulating portion 144 in a direction opposite that of bearing 142.

Bearing 142 is substantially cylindrical and elongate so as to extend through tibial insert 130 and into bearing bushing 120 while being rotatable therein.

Articulating portion 144 includes a convex articular surface 146 corresponding to the concavity of articular surface 132 of tibial component 130. In addition, the thickness of articulating portion 144 is generally greater at a posterior extent thereof than at an anterior extent thereof. This is at least partially due to articular surface 146 having a greater slope at an anterior extent thereof than the posterior extent thereof.

Head portion 145 is semi-rectangular and rounded at a proximal end thereof. Head portion 145 is sized to be received within a recess 146 of femoral component 180. Head portion 145 also includes a first opening 147 which extends through an anterior surface thereof in an anterior/posterior direction. This first opening 147 is sized to receive post 16 of guide 10 and bumper extension 152 of bumper 150. Head portion 145 also includes a second opening 148 which extends through lateral and medial surfaces thereof in a lateral/medial direction transverse to first opening 147. Second opening 148 is preferably disposed more proximal than first opening 147 and is sized to receive axle 160. Additionally, in some embodiments, particularly in embodiments where bumper extension 152 is notched (described further below), first openings 147 may at least partially intersect second opening 148.

In some embodiments, baseplate component 110 does not include bearing component 140 and bearing bushing 120. In such an embodiment, tibial insert 130 remains part of the tibial component such that tibial insert 130 is the articular portion connected to baseplate 112 of baseplate component 110. In this regard, head 145 may be integral with and extend from baseplate portion 112 and articular potion (i.e. tibial insert 130). As such, insert 130 may have a notch or opening that allows head 145 to pass therethrough.

Bumper 150 includes a bumper portion 154 and bumper extension 152. Bumper portion 154 has a distal surface 156 configured to rest on a proximal surface of articulating portion 144 of bearing component 140 and a proximal surface 158 configured to abut a distal anterior portion of femoral component 180. Bumper portion 150 may be made from resilient biocompatible materials which can absorb impact from femoral component 180 and compression between femoral component 180 and bearing component 140 over repeated cycles of knee hyperextension.

Bumper extension 152 is substantially cylindrical and sized to extend within first opening 147 of bearing component 140. Bumper extension 152 may also include a rounded notch (not shown) on a proximal surface thereof extending in a direction transverse to a longitudinal axis of bumper extension 152. Such notch may be shaped and positioned along bumper extension 152 so that when extension 152 is inserted into first opening 147 of bearing component 140, axle 160 can be inserted through second opening 148 and be partially disposed within the notch, thereby preventing extension 152 from being removed from first opening 147.

Axle 160 is substantially cylindrical and is sized to be received by axle bushings 170 and second opening 148 of bearing component 140.

Axle bushings 170 are also cylindrical and have openings 172 extending therethrough along a length thereof. Bushings 170 also include a flange 174 at one end thereof. Bushings 170 are sized to fit within transverse openings 184 of femoral component 180 (described further below) while flange 174 is sized to prevent such bushings 170 from passing all the way through transverse openings 184.

Femoral component 180 generally includes inner bone contact surfaces, a stem portion 188, a recess 186, transverse openings 184, and a distal surface 190. Generally TKA prostheses include five inner contact surfaces each corresponding with one of a posterior, anterior, distal, anterior chamfer, and posterior chamfer resected surfaces of a distal femur. While a femoral component according to the present invention can have five of such inner surfaces, femoral component 180 includes three inner contact surfaces in order to allow for femoral component 180 to have sufficient thickness at a posterior portion thereof for transverse openings 184 to extend therethrough.

Stem portion 188 extends from the second and/or third surfaces and may include an opening therein for receipt of a modular stem (not shown). Stem portion 188 may have a porous outer surface to promote bony ingrowth or cement adhesion.

Recess 186 extends through a posterior portion of femoral component 180 adjacent to stem portion 188 and through first inner surface 181. Recess 186 at least partially defines first (lateral) and second (medial) condylar portions 185 and 187. First and second condylar portions 185, 187 each define a curved distal surface. The curved distal surface of first and second condylar portions 185, 187 may be a convex curvature.

Transverse openings 184 extend through first and second condylar portions 185, 187 and intersect recess 186. Openings 184 are aligned such that they are concentric with each other and are sufficiently large to receive axle bushings 170 while being smaller than flanges 174 of axle bushings 170.

Distal surface 190 is curved in a sagittal plane and is primarily configured for articulation with a patella or patellar prosthesis. As such, distal surface 190 may have an intercondylar groove for patellar tracking to prevent lateral or medial subluxation of a patella. The distal surface 190 of femoral component 180 and the distal surfaces of the first and second condylar portions 185, 187 may include a plurality of portions each defined by a different radius of curvature. The distal surface of the first and second condylar portions 185, 187 may each have an anterior section and a posterior section. The anterior section may be curved such that it defines a first radius of curvature. The posterior section may be curved such that it defines a second radius of curvature different than the first radius of curvature. An exemplary femoral component having multiple radii of curvature can be found in U.S. Publication No. 2017/0035572, the disclosure of which is incorporated by reference herein in its entirety.

FIGS. 1 and 2A-2C depict the assembly guide 10. Assembly guide 10 is configured for aligning a femoral component and tibial component of a hinge knee prosthesis such that an axle can be easily connected thereto, as described in more detail below. In this regard, guide 10 is configured to be inserted between femoral component 180 and the tibial component and serves as a temporary shim or wedge to assist in assembling the final implant, such as when at a 90 degree angle of flexion, for example.

Guide 10 generally includes first and second body portions 24, 26, first and second wedge portions 12, 14, and a bridge 22. Bridge 22 is connected to and extends between first and second body portions 24, 26. First and second wedge 12, 14 are respectively connected to first and second body portions 24, 26 and extend in a first direction therefrom. The first and second wedges 12, 14 are separated by a recess 28. Recess 28 is configured for receipt of head portion 145 of the bearing component 140, as discussed below. As mentioned above, Bridge 22 is connected to and extends between the first and second body portions 24, 26. In this regard, bridge 22 at least partially defines recess 28.

First and second wedges 12, 14 each have a thickness defined between a respective proximal surface 18, 20 and distal surface 13, 15 and extend in a second direction transverse to the first direction. According to the depicted embodiment, the first direction is a posterior direction such that first and second wedges 12, 14 respectively extend posteriorly from first body portion 24 and second body portion 26. The thicknesses of wedge portions 12, 14 are configured such that they can be wedged between femoral component 180 and the tibial component so as to support femoral component 180 and so that wedge portions 12, 14, by virtue of their thicknesses, align openings 148 and 184 to allow axle 160 to be easily advanced therein.

To help facilitate support of femoral component 180, in this regard, proximal surfaces 18, 20 of first and second wedges 12, 14 are curved so as to correspondingly engage a respective condyle of a femoral component, when guide 10 is positioned between femoral component 180 and the tibial component. Thus, curved proximal surfaces 18, 20 have a geometry configured to correspond to the geometry of distal surface 190 of femoral component 180 such that the curved proximal surfaces 18, 20 correspond to a curvature of respective condyles of femoral component 180, such as when at a 90 degree angle of femoral flexion, for example. According to one embodiment, the curved proximal surfaces 18, 20 each have a concave curvature equal to a radius of curvature of a convex distal surface of the condylar portions of femoral component 180. Where femoral component 180 includes multiple curved portions that each have their own respective radius of curvature different from the other, curved proximal surfaces 18, 20 may be curved to correspond to one of such curved portions. For example, where distal surface 190 of femoral component 180 has an anterior curved portion and a posterior curved portion each with a different radius of curvature, curved proximal surfaces 18, 20 may have a curvature corresponding to that of the posterior portion. In this respect, curved proximal surfaces 18, 20 would be congruent with a posterior aspect of respective condyles 185 and 187, but would be incongruent with an anterior aspect of such condyles 185, 187. Thus, curved surfaces 18, 20 may only fully engage femoral component 180 when femoral component 180 is at a particular flexion angle relative to the tibial component, as best shown in FIG. 3A. Such flexion angle may be 90 degrees for example. In this regard, guide 10 may constrain femoral component 180 relative to the tibial component during assembly of axle 160 which may make assembling axle 160 to such components easier. In addition, curved surfaces 18, 20 being congruent to a posterior aspect of femoral component 180 and incongruent relative to an anterior aspect helps align openings 148 and 184 in an anteroposterior direction as well as a superior-inferior direction since full engagement of guide 10 is achieved in a particular alignment between femoral and tibial components and allows the surgeon to identify when such alignment is achieved.

Distal surfaces 13 and 15 are configured to engage and rest upon a proximal end of the tibial component. Thus, in the embodiment depicted, distal surfaces 13 and 15 are configured to engage a proximal side of articular portion 144 of bearing component 140 and, thus, may be planar. However, in other embodiments where femoral component 180 directly articulates with tibial insert 130, distal surfaces 13 and 15 may be convexly curved similar to articular surface 146 so as to correspond to the concave curvatures of insert 130 so that guide 10 can rest directly upon insert 130. In even further embodiments, distal surfaces 13 and 15 may be configured to rest directly upon a proximal surface of baseplate portion 112.

Guide also includes a post 16 extending from bridge 22. Post 16 extends in the same direction as first and second wedges, 12, 14 such that post 16 extends in a posterior direction into recess 28. Post 16 is substantially cylindrical and sized to extend within an opening 147 of head 145, discussed in more detail below. However, in some embodiments, post may be rectangular shaped or the like.

Figure 3B:
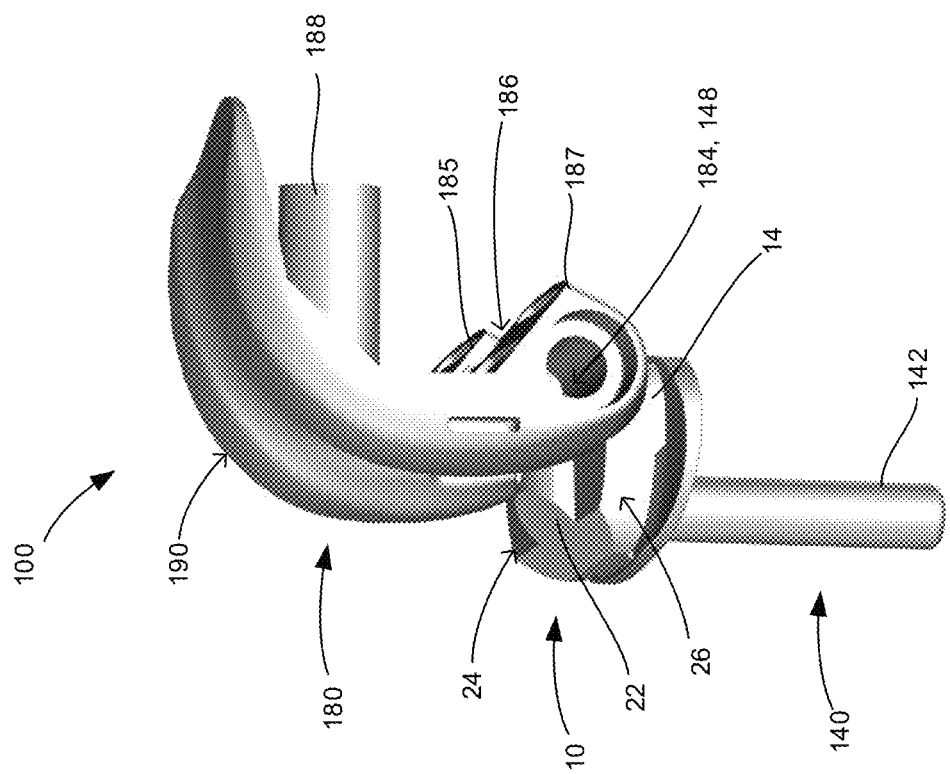
FIG. 3B is a perspective view of the partial assembly of FIG. 3A.
Figure 3A:
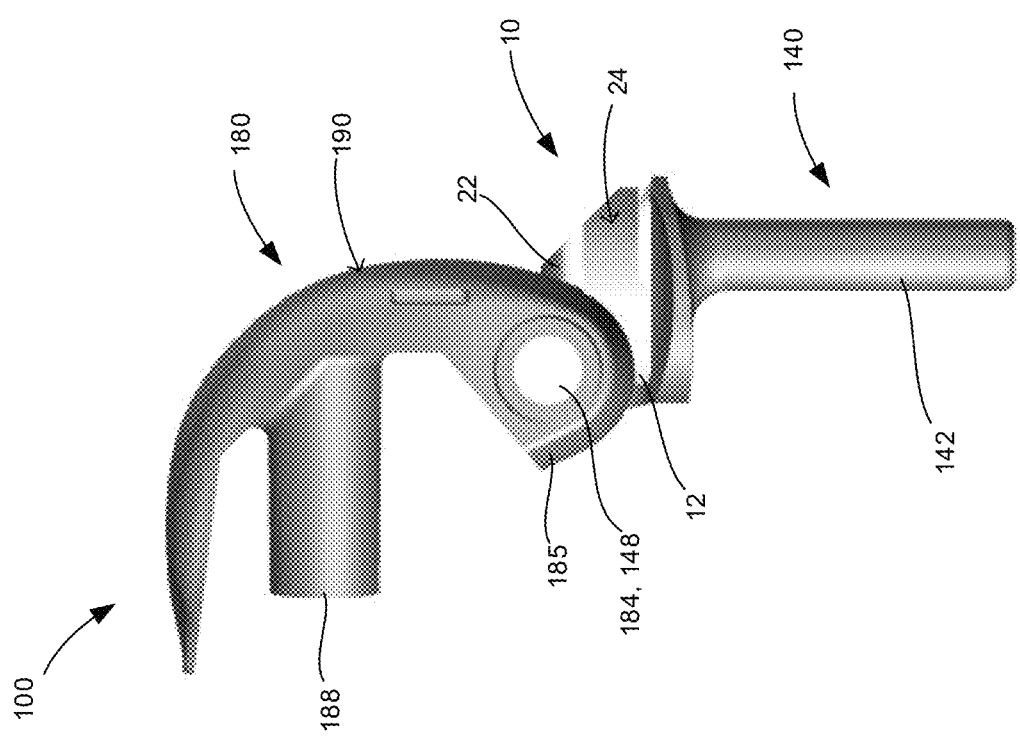
FIG. 3A is a side view of a partial assembly of the total knee prosthesis system.

FIGS. 3A and 3B depict guide 10 positioned between femoral component 180 and the tibial component in a fully engaged position. More particularly, guide 10 is positioned between bearing component 140 and femoral component 180 such that wedge portions 12 and 14 are disposed between respective condyles 185, 187 of femoral component and bearing component 140 and so that distal surface 190, as defined by such condyles 185 and 187, congruently engage curved proximal surfaces 18, 20 of guide 10. In the embodiment depicted, such congruent contact occurs when femoral component 180 is at a flexion angle of 90 degrees relative to the tibial component. Moreover, post 16 is received in post opening 147 of head 145. When post is fully received within post opening 147, the surgeon is assured that guide 10 has appropriately positioned femoral component 180 the anteroposterior direction relative to head 145 so that openings 148 and 184 align in the anteroposterior direction. Post 16 also helps prevent unintended movement of femoral component 180 relative to head 145. The thicknesses of wedge portions 12 and 14 further align femoral component 180 relative to head 145 in a superior-inferior direction so that openings 148 and 184 align in such direction. Thus, in this position, axle 160 may be easily slide into openings 148 and 184.

In a method of assembling prosthesis 100, femoral component 180 is connected to a resected distal femur and baseplate component 110 is connected to a proximal tibia. Bearing bushing 120 is inserted into opening 118 of baseplate component 110. Tibial insert 130 is then attached to proximal surface 111 of baseplate 112. Thereafter, bearing 142 is inserted through opening 134 in tibial insert 130 and into bearing bushing 120 until articular surface 146 of bearing component 140 contacts articular surface 132 of tibial insert 130. The convexity of articular surface 146 of bearing component 140 and concavity of articular surface 132 of tibial insert 130 help bearing component 140 settle into proper alignment.

Axle bushings 170 are inserted into respective transverse openings 184 of femoral component 180 such that flanges 174 face each other and are disposed adjacent to intercondylar recess 186. The head portion 145 of the tibial component is positioned into the intercondylar recess 186 of femoral component 180. Guide 10 is then inserted between baseplate component 110 and femoral component 180. As guide 10 is inserted between tibial component and femoral component, post 16 of guide 10 is inserted into post opening 147 of bearing component 140.

Inserting guide 10 between baseplate component 110 and femoral component 180 includes wedging guide 10 between the baseplate component 110 and femoral component 180 so that proximal surfaces 18, 20 of guide 10 support femoral component 180 and the distal surfaces 13, 15 of guide 10 rest on component 140, as best shown in FIGS. 3A and 3B. However, prior to inserting guide 10 into the space between femoral component 180 and component 140, femur, along with femoral component 180, may be positioned at 90 degrees of flexion relative to the tibia or any other appropriate flexion angle. As femoral component 180 is supported by the proximal surfaces 18, 20 of guide 10, first and second condylar portions 185, 187 are seated on first and second wedges 12, 14, respectively. The curvature of the distal surface of the first and second condylar portions 185, 187 may be such that femoral component 180 can only be seated properly on guide 10 at one angle of flexion. The angle of flexion may be 90 degrees.

After guide 10 is inserted between baseplate component 110 and femoral component 180, transverse openings 184 of femoral component 180 are aligned with second opening 148 of the femoral component. Axle 160 is then inserted through axle bushings 170 and bearing component 140, thereby coupling femoral component 180 to the tibial component. Guide 10 is then removed and bumper 150 may be inserted in its place. Bumper 150 helps prevent hyperextension of femoral component 190.

The above described system includes a hinge knee prosthesis 180 in which condyles 185, 187 of the femoral component 190 do not directly articulate with the tibial component, such as with the tibial insert 130. In this regard, when guide 10 is used to align femoral component 180 with the tibial component for receipt of axle 160, guide 10 is positioned between femoral component 190 and articular portion 144 of bearing component 140 such that guide 10 rests on articular portion 144, which itself articulates with insert 130. However, it should be understood that guide 10 can work with other hinge knee configurations. For example, in some embodiments, a femoral component, such as component 180, may have condyles that directly contact and articulate with a tibial insert, such as insert 130. In such embodiments, there may be no articular portion 144. Thus, guide 10 may be configured, as described above, to rest on the tibial insert while supporting the femoral component so that an axle can be connected thereto. In such embodiments, guide 10 may or may not include post 16.

In another method of assembling a hinge knee prosthesis in which embodiments as immediately described above are assembled, a bearing component that includes a bearing and head, such as bearing 142 and head 145, but without portion 144, is connected to baseplate component 110. In such an embodiment, head 145 would extend from the proximal most surface of baseplate component 110. Head 145 is similarly inserted into the intercondylar space 186 of femoral component 180. However, unlike in the method described above, insert 10 is inserted between the tibial component and femoral component 180 so that guide 10 rests on the tibial insert, such as insert 130 or another insert that includes discrete concave condylar portions as is generally understood in the art. Femoral component 180 may similarly be positioned at a predetermined angle of flexion for guide 10 to effectively operate. Once a head opening 148 and opening 184 are aligned, axle 160 may be inserted to connect femoral component 180 to the tibial component 110.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A total knee prosthesis system, comprising:
   an axle;
   a tibial component having a baseplate portion, an articular portion connected to the baseplate portion, and a protruding portion extending from the baseplate and articular portions, the protruding portion having a first axle opening for receipt of the axle;
   a femoral component having a distal surface and a second axle opening for receipt of the axle; and
   a guide having first and second wedges each having a thickness configured to be located between the tibial component and the femoral component such that, when the first and second wedges are located between the tibial component and the femoral component, the first and second wedges align the first axle opening with the second axle opening for receipt of the axle therein.

2. The system of claim 1, wherein the guide includes a post extending therefrom and the protruding portion includes a post opening, the post opening of the tibial component being configured to receive the post.

3. The system of claim 1, wherein, when the guide is located between the tibial component and the femoral component, a distal end surface of the guide engages with the tibial component.

4. The system of claim 1, wherein the first and second wedges each have a curved proximal surface.

5. The system of claim 2, wherein the distal surface of the femoral component has a plurality of portions each defined by a different radius of curvature, and the curved proximal surface of each of the first and second wedges having a radius of curvature matching the radius of curvature of a first of the plurality of portions of the distal surface of the femoral component.

6. The system of claim 1, wherein the guide has a fully seated position when located between the tibial and femoral components and the guide can only achieve the fully seated position at one angle of flexion.

7. A total knee prosthesis system, comprising:
   a femoral component having first and second condylar portions each defining a convex distal surface, the first and second condylar portions further defining an intercondylar recess therebetween and a first axle opening extending therethrough, the axle opening being in communication with the intercondylar recess;
   a tibial component defining a concave proximal surface;
   an axle;
   a coupling component coupled to the tibial component and having a head portion extending from the tibial component, the head portion defining a second axle opening; and
   a wedge shaped assembly guide having an upper surface, a lower surface, and a thickness therebetween,
   wherein, when the head portion is received within the intercondylar recess and the wedge shaped assembly guide is interposed between the tibial component and femoral component, the thickness of the assembly guide positions the femoral component such that the first axle opening coaxially aligns with the second axle opening, and
   wherein the axle is configured to be inserted into the coaxially aligned first and second axle openings.

8. The system of claim 7, wherein the tibial component includes a baseplate member and a polymer insert, the polymer insert defining the concave proximal surface.

9. The system of claim 7, wherein the wedge shaped assembly guide includes first and second guide portions and a guide recess extending therebetween, the guide recess being configured to receive the head portion of the coupling component.

10. The system of claim 9, wherein the wedge shaped assembly guide includes a bridge connected to and extending between the first and second guide portions, the bridge at least partially defining the guide recess.

11. The system of claim 10, wherein:
the wedge shaped assembly guide includes a post extending from bridge and into the guide recess, and the head portion defines a post opening configured to receive the post.

12. The system of claim 10, wherein the upper surface of the wedge shaped assembly guide includes a first concave portion on the first guide portion and a second concave portion on the second guide portion.

13. The system of claim 12, wherein the first concave portion has a radius of curvature equal to a radius of curvature of the convex distal surface of the first condylar portion.

14. The system of claim 12, wherein the distal surface of the first condylar portion has an anterior section and a posterior section, the anterior section having a first radius of curvature, the posterior section having a second radius of curvature, the first and second radii of curvature being different.

15. The system of •claim 14, wherein the first concave portion of the wedge shaped assembly guide has a third radius of curvature equal to the second radius of curvature.

\* \* \* \* \*